United States Patent
Morman et al.

[11] Patent Number: 6,117,803
[45] Date of Patent: Sep. 12, 2000

[54] PERSONAL CARE ARTICLES WITH ABRASION RESISTANT MELTBLOWN LAYER

[75] Inventors: Michael Tod Morman, Alpharetta, Ga.; Thomas Walter Odorzynski, Green Bay, Wis.; Wanda Walton Jackson, Alpharetta; Gregory Todd Sudduth, Cumming, both of Ga.

[73] Assignee: Kimberly-Clark Worldwide, Inc., Neenah, Wis.

[21] Appl. No.: 08/920,497

[22] Filed: Aug. 29, 1997

[51] Int. Cl.⁷ .................................................. B32B 5/26
[52] U.S. Cl. ...................... 442/381; 442/351; 442/382; 442/392; 442/394; 442/400; 442/401; 604/358; 604/372; 604/378
[58] Field of Search .................... 442/351, 381, 442/382, 392, 394, 400, 401; 604/358, 370, 372, 378

[56] References Cited

U.S. PATENT DOCUMENTS

| | | |
|---|---|---|
| 4,041,203 | 8/1977 | Brock et al. . |
| 4,659,609 | 4/1987 | Lamers et al. . |
| 4,774,125 | 9/1988 | McAmish . |
| 4,828,556 | 5/1989 | Braun et al. ............................ 604/365 |
| 4,910,064 | 3/1990 | Sabee . |
| 5,200,246 | 4/1993 | Sabee . |
| 5,219,633 | 6/1993 | Sabee . |
| 5,429,854 | 7/1995 | Currie et al. . |
| 5,460,884 | 10/1995 | Kobylivker et al. . |
| 5,492,751 | 2/1996 | Butt, Sr. et al. . |
| 5,508,102 | 4/1996 | Georger et al. . |
| 5,547,746 | 8/1996 | Burton, Sr. . |
| 5,589,258 | 12/1996 | Maddern et al. . |
| 5,624,425 | 4/1997 | Gray et al. . |

FOREIGN PATENT DOCUMENTS

| | | |
|---|---|---|
| 0742305 | 11/1996 | European Pat. Off. . |
| 0775572 | 5/1997 | European Pat. Off. . |
| 2293573 | 4/1996 | United Kingdom . |
| 9501474 | 1/1995 | WIPO . |
| 9706945 | 2/1997 | WIPO . |
| 97/16148 | 5/1997 | WIPO . |

Primary Examiner—Christopher Raimund
Attorney, Agent, or Firm—Pauley Petersen Kinne & Fejer

[57] ABSTRACT

A diaper outer cover of a layered nonwoven material having an outer meltblown fiber layer of a meltblown material having an average basis weight in the range of about 1 g/m² to about 7 g/m² disposed on an inner nonwoven material layer, preferably a spunbond web.

20 Claims, 1 Drawing Sheet

PERSONAL CARE ARTICLES WITH ABRASION RESISTANT MELTBLOWN LAYER

FIELD OF THE INVENTION

This invention relates to a layered nonwoven material comprising an abrasion-resistant meltblown material layer and a nonwoven material layer, such as a spunbond, where the nonwoven material layer typically is more resistant to abrasion than a meltblown material layer. More particularly, this invention is directed to limited use or disposable items, such as disposable diapers and other disposable personal care articles, employing such a material. In addition, this invention is directed to a method for producing such materials.

BACKGROUND OF THE INVENTION

This invention is directed to layered nonwoven materials comprising an abrasion resistant meltblown layer, which materials are suitable for use as outer covers for personal care articles such as disposable diapers and other disposable personal care articles, as well as medical garments, such as surgical gowns, medical drapes, and the like.

Layered nonwoven materials are widely used in a variety of applications, for example, such as components of absorbent articles such as disposable diapers, adult incontinence garments, and sanitary napkins, and in medical garments, such as surgical gowns, surgical drapes, sterilization wraps, and surgical face masks.

Layered nonwoven materials can be created for a variety of specific end uses by combining two or more nonwoven webs of different types. Thus, layered nonwoven materials have been developed to provide a barrier to penetration by contaminants such as microorganisms. Barrier nonwoven materials of this type typically include one or more microfibrous polymer layers, such as meltblown webs, combined with one or more layers of another type of nonwoven web, such as, for example, a spunbonded continuous filament fabric or a fabric of staple fibers. In known layered materials such as these, the outer layers function as strength reinforcing layers during use so as to protect the weaker meltblown web from excessive stresses and potential damage. Indeed, in order to protect the meltblown web from abrasion, it is normally disposed between two layers of another material, such as spunbond, which has a higher abrasion resistance, in a spunbond/meltblown/spunbond laminate. Such layered materials, thus, have outside spunbonded layers which are durable and an internal meltblown barrier layer which is porous but which, in combination with the spunbond layers, inhibits the strike through of liquids or the penetration of bacteria from the outside of the layered material to the inside.

The use of microfiber webs in applications where barrier properties are desired is known in the prior art. Microfibers are fibers having a denier per filament of from less than 0.006 to about 0.664. Microfiber webs are often referred to as meltblown webs as they are usually made by a meltblown process. It is generally recognized that the use of relatively small diameter fibers provides high repellency or filtration properties without undue compromise of breathability. Microfiber web fabrics made prior to now and intended for use as barriers in personal care articles and medical garments have been composites of microfiber webs laminated or otherwise bonded to spunbonded thermoplastic fiber webs, or films, or other reinforcing webs which provide the requisite strength. An important requirement for both non-woven materials as well as personal care articles and medical garments is abrasion resistance. In the case of disposable diapers, resistance to surface abrasion is particularly important when a child is playing outdoors without clothing covering the diaper. Thus, an outer layer of a spunbonded fiber web, film or other reinforcing web is conventionally used to provide surface abrasion resistance in meltblown fiber products.

Personal care absorbent articles, such as disposable diapers, training pants, incontinence wear and feminine hygiene products, utilize nonwoven materials for many purposes such as liners, transfer layers, absorbent media, backings, and the like. For many such applications, the barrier properties of the nonwoven material play an important role. Disposable garments utilized for the absorption and containment of urine or other body exudates generally comprise a liquid pervious body side liner and a fluid impervious backing sheet or outer cover with an absorbent material disposed therebetween.

We have found that a spunbond material with a thin layer of meltblown fibers sprayed on it has about the same abrasion resistance as the spunbond itself. In view of the known generally lower resistance to abrasion of meltblown materials, this is, indeed, an unexpected and surprising finding. Much like a thin layer of paint protects a surface, compared to a very thick layer of paint which readily abrades, the thin meltblown layer acts as a protective coating, supported from below by the nonwoven web material it is coating. As a result of this discovery, meltblown fabrics, which have good barrier properties, making them particularly suited to use in personal care articles such as diapers, but which heretofore, due to their lack of strength and resistance to abrasion have, of necessity, been laminated between layers of nonwoven webs having the requisite strength, including resistance to abrasion, can now be used as the outer layer on such personal care articles, such as diaper outer covers. This, in turn, reduces the costs associated with production of these articles by eliminating the need for an additional outer nonwoven layer to protect the meltblown layer.

Nonwoven fabrics with improved abrasion resistance employing microfiber webs are taught by U.S. Pat. No. 4,774,125 which discloses a surface abrasion resistant material including a surface veneer of meltblown fibers having an average fiber diameter of greater than 8 microns (0.42 denier per filament for polypropylene) and in which 75% of the fibers have a fiber diameter of at least 7 microns (0.33 denier per filament for polypropylene) bonded to a meltblown core web. Such a material is indicated to be suitable for use as a medical fabric but, due to the lack of an absorbent layer, would not be suitable for use in personal care absorbent articles.

Accordingly, it is an object of this invention to provide an outer cover for personal care articles, such as diapers, having an outer meltblown layer which is resistant to abrasion, thereby permitting these items to be worn without additional layers, such as clothing, covering them to protect them from damage.

SUMMARY OF THE INVENTION

This and other objects of this invention are achieved by an outer cover for personal care articles such as diapers comprising a layered nonwoven material comprising an outer, or veneer, meltblown fiber layer of a meltblown material having an average basis weight in a range of about 1 g/m$^2$ to about 7 g/m$^2$ disposed on an inner nonwoven material layer. The inner nonwoven material layer suitable for use in this invention normally has a higher resistance to abrasion than a single meltblown layer. In accordance with a particularly preferred embodiment of this invention, the inner nonwoven material layer is a spunbond layer. To further provide liquid imperviousness, a liquid impervious film layer may be laminated to the face of the inner nonwoven material layer facing away from said meltblown fiber layer.

The outer surface of the spunbond/meltblown layered material in accordance with one embodiment of this invention has an abrasion resistance corresponding to the abrasion resistance of spunbond alone. That is, the outer meltblown material layer has an abrasion resistance which corresponds to the abrasion resistance of spunbond material layers alone. This is particularly unexpected because meltblown webs by themselves are known to have a lower resistance to abrasion than other nonwoven webs such as spunbonds. In addition, the nonwoven layered material provides a significant improvement to personal care articles when used as a component of clothlike outer covers in, for example, diapers, where the meltblown material is the outer layer of the diaper outer cover, including greater opacity than spunbond material alone. Since the introduction of clothlike outer covers, consumers have reported the tendency of such outer covers to stain when contacted by food, drinks, and/or liquids. In addition, the outer covers have been reported to soil easily and snag on twigs and the like when the child is playing outdoors without clothing covering the diaper. The diaper outer cover of this invention, where the outer face is a meltblown material layer, in addition to being abrasion resistant, is also resistant to stain and snagging by sticks, hooked materials, and the like. A further advantage of the outer cover of this invention is that the outer surface, that is the meltblown layer, is more readily printed on than other nonwoven materials.

While the invention will be described in connection with personal care articles, and in particular, diapers, it will be understood that the layered nonwoven material of this invention is suitable for use in a variety of articles such as surgical gowns and drapes, car covers, sterile wraps, etc.

BRIEF DESCRIPTION OF THE DRAWINGS

This invention will be better understood from the following detailed description taken in conjunction with the drawings wherein.

DEFINITIONS

Figure 1:
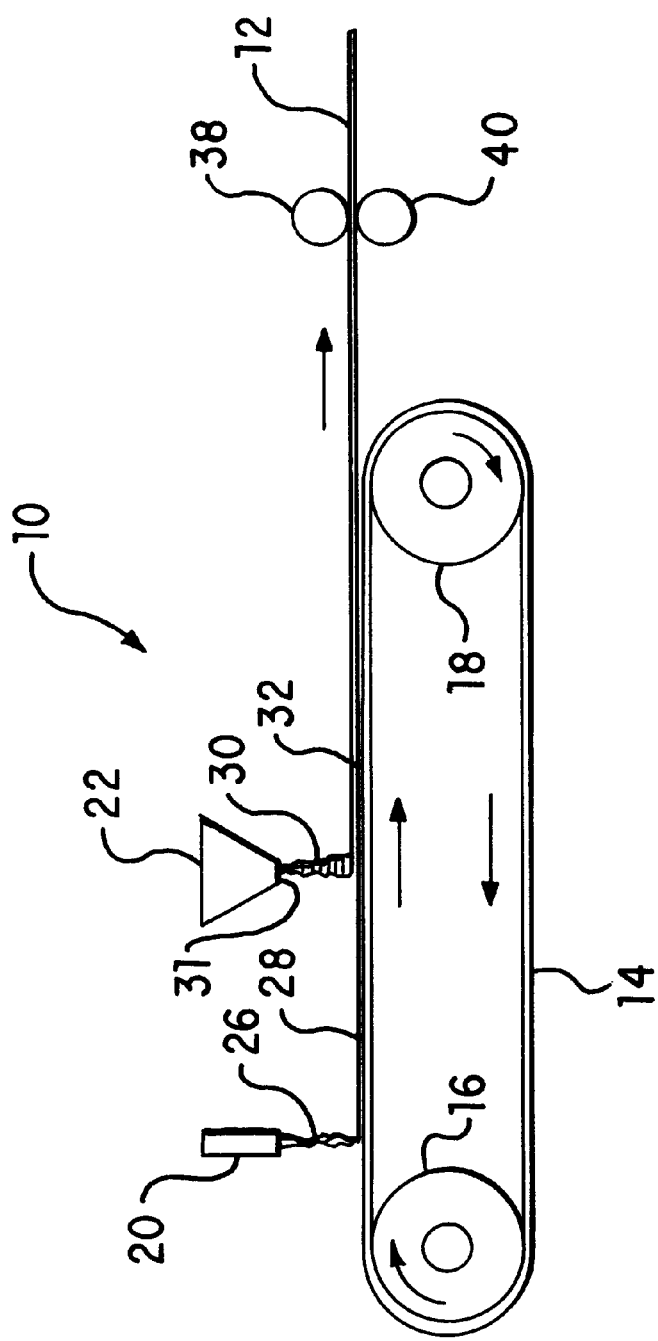
FIG. 1 is a schematic diagram of a forming machine used to make the nonwoven layered material including the meltblown barrier layer of this invention.

As used herein, the term "nonwoven web" means a web that has a structure of individual fibers or threads which are interlaid, but not in an identifiable repeating manner. Nonwoven webs have been, in the past, formed by a variety of processes such as, for example, melt-blowing processes, spunbonding processes, and bonded carded web processes.

As used herein, the term "spunbonded fibers" refers to small diameter fibers which are formed by extruding a molten thermoplastic material as filaments from a plurality of fine, usually circular, capillaries of a spinnerette with the diameter of the extruded filaments then being rapidly reduced as by, for example, eductive drawing or well-known spunbonding mechanisms.

As used herein, the term "polymer" generally includes, but is not limited to, homopolymers, copolymers, such as, for example, block, graft, random and alternating copolymers, terpolymers, etc., and blends and modifications thereof. Furthermore, unless otherwise specifically limited, the term "polymer" includes all possible geometrical configurations of the material. These configurations include, but are not limited to, isotactic, syndiotactic, and random symmetries.

As used herein, the term "meltblown fibers" means fibers formed by extruding a molten thermoplastic material through a plurality of fine, usually circular, die capillaries as molten threads or filaments into a high velocity gas, for example, air, stream which attenuates the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers.

DESCRIPTION OF PREFERRED EMBODIMENTS

This invention is generally directed to an outer cover for personal care absorbent articles such as disposable diapers, training pants, incontinent wear and feminine hygiene products as well as for industrial garments, medical garments, medical drapes, and the like. The outer cover of this invention comprises a nonwoven layered material comprising an outer meltblown fiber layer of a meltblown material having an average basis weight in a range of about 1 g/m$^2$ to about 7 g/m$^2$ disposed on an inner nonwoven material layer. In accordance with a preferred embodiment, the basis weight of the meltblown material is in the range of 3 g/M$^2$ to about 7 g/m$^2$, most preferably about 5 g/m$^2$.

The inner nonwoven material layer is preferably a spunbond web formed from spunbonded fibers. Because spunbond webs have no barrier properties, it is preferred that the outer layer of the diaper outer cover have at least some of the requisite barrier properties. The layered nonwoven material of this invention comprising a meltblown layer disposed on a spunbond layer resists liquid penetration better than spunbond alone. However, to ensure against liquid penetration, the diaper outer cover in accordance with one embodiment of this invention further comprises a film layer laminated to the inner facing face of the spunbond layer, that is, the face of the spunbond layer facing away from the meltblown layer.

A diaper outer cover also should have a substantial resistance to abrasion and snagging so as to be able to withstand the harsh conditions of the environment in which a child wearing the diaper is playing. Accordingly, in addition to having an average basis weight in the range of about 1 g/m$^2$ to about 7 g/m$^2$, we have found that microfiber size of the meltblown material is also a consideration. In accordance with one embodiment of this invention, the outer meltblown layer of the diaper outer cover of this invention is comprised of microfibers having a denier per filament in the range of about 0.01 to about 0.67. In accordance with a particularly preferred embodiment of this invention, the microfibers of the outer meltblown layer have a denier per filament of less than about 0.06. Microfibers having smaller deniers are preferred because they provide more uniform layers. For example, for a meltblown fiber layer having a basis weight of about 3.0 g/m$^2$, a 0.035 denier fiber has about twelve times the length of fibers per unit area as a 0.42 denier fiber. Thus, the longer the fibers per unit area, the more uniform will be the resulting material layer.

Accordingly, the outer meltblown fiber layer of the material of this invention has a uniformity such that no ½-inch diameter circle of the meltblown fiber layer has a basis weight of less than about 1 g/m² and greater than about 7 g/m².

Abrasion resistance of the material of this invention is determined, in general, in accordance with the methods of ASTM Standard D-1175, "Abrasion Resistance of Textile Fabrics". These methods cover the determination of abrasion resistance of textile fabrics using oscillatory cylinder and uniform abrasion procedures. These methods are used in determining the abrasion resistance of specified textile fabrics in a controlled manner by machines which subject specimens to unidirectional rubbing action under known conditions of pressure, tension, and abrasive action or rub specimens uniformly in all directions in the plane of the surface of the specimen about every point in it. Testing of the material of this invention was conducted using the Taber method employing a rotary platform, double head abraser. The results of the abrasion tests conducted on the material of this invention are shown in Table 1.

TABLE 1

| Anvil # of cycles | Face # of cycles |
| --- | --- |
| 7.000 | 6.000 |
| 5.000 | 5.000 |
| 5.000 | 6.000 |
| 6.000 | 4.000 |
| 7.000 | 6.000 |
| 4.000 | 5.000 |
| 7.000 | 4.000 |
| 6.000 | 6.000 |
| 7.000 | 4.000 |
| 6.000 | 6.000 |
| Mean 6.000 | 5.200 |
| Std. Dev. 1.054 | 0.919 |

The data in Table 1 were collected on a material comprising a layer of spunbond filaments having a basis weight of about 17 g/m² and a layer of meltblown fibers formed thereon having a basis weight of about 4 g/m². As shown in Table 1, the spunbond face, designated as "FACE" had a Taber abrasion of 5.2±0.9 cycles while the meltblown face, designated as "ANVIL", had a Taber abrasion of 6.0±1.0. That is, the meltblown face had an abrasion resistance greater than the abrasion resistance of the spunbond face, spunbond conventionally having a higher abrasion resistance than meltblown and, thus, conventionally being used to protect meltblown fibers from abrasion.

Another consideration for applications of the layered nonwoven materials of this invention is the overall weight of the material. That is, it is desirable that the material be as light weight as possible. Accordingly, the layered nonwoven materials of this invention comprising a spunbond layer and a meltblown layer preferably have an average basis weight of less than about 23 g/m². In accordance with one particularly preferred embodiment, the average basis weight of the spunbond layer is about 17.3 g/m² and the average basis weight for the meltblown layer is about 4.0 g/m².

FIG. 1 is a schematic diagram of a forming machine used to make the nonwoven layered material including the outer meltblown barrier layer in accordance with this invention. Forming machine 10 is used to produce a layered nonwoven material 12 having an outer fine fiber meltblown barrier layer 32 and an inner spunbond layer 28 in accordance with this invention. In particular, forming machine 10 consists of an endless formations forming belt 14 wrapped around rollers 16 and 18 so that the belt is driven in the direction shown by the arrows. Forming machine 10 has two stations, spunbond station 20 and meltblown station 22.

Spunbond station 20 is a conventional extruder with spinnerettes which form continuous filaments 26 of a polymer at a temperature of about 440° F. and deposit those filaments onto forming belt 14 in a random interlaced fashion. Spunbond station 20 may include one or more spinnerettes depending on the speed of the process and the particular polymer being used. Forming spunbonded materials conventional in the art and the design of such a spunbonded forming station is well within the ability of those of ordinary skill in the art.

Meltblown station 22 consists of a die 31 which is used to form microfibers 30. As the thermoplastic polymer at a temperature of about 510° F. exits the die 31, high pressure fluid, usually air, at a temperature of about 540° F., attenuates and spreads polymer stream to form microfibers 30. The microfibers 30 are randomly deposited on top of spunbond layer 28 and form meltblown layer 32. The construction and operation of meltblown station 22 for forming microfibers 30 and meltblown layer 32 is generally considered conventional, and the design and operation thereof are well within the ability of one skilled in the art. The resulting layers of nonwoven material are then fed through calender rolls 38 and 40. Critical to the bonding process is the requirement that the smooth calender roll, or anvil roll, (in FIG. 1, this is calender roll 38) be on the same side of the nonwoven material as the meltblown layer due to the fact that the meltblown layer will often stick to the pattern roll (in FIG. 1, this is calender roll 40) in a calender unit while the probability of sticking to the smooth anvil roll is much lower. To further reduce the probability of sticking and still get good bonding, the temperature of the smooth anvil roll 38 is reduced to about 240° F. while the pattern roll 40 is maintained at a temperature of about 285° F. While in the process diagram of FIG. 1, the anvil roll 38 is on the top side of the nonwoven material so as to contact the meltblown layer which has been deposited onto the spunbond layer, it will be apparent to those skilled in the art that the meltblown layer can be formed first on belt 14 after which the spunbond layer is applied. In this case, the anvil roll would be on the bottom side of the nonwoven material so as to contact the meltblown layer which, in this configuration, is on the underside of the layered nonwoven material.

Figure 2:
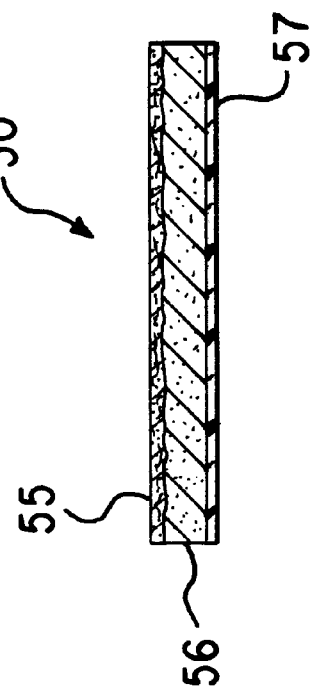
FIG. 2 is a cross-sectional view of a layered nonwoven material in accordance with one embodiment of this invention.

FIG. 2 is a cross-sectional view of a layered nonwoven material 50 in accordance with one embodiment of this invention comprising outer meltblown fiber layer 55 disposed on inner nonwoven material layer 56 and having a film layer 57 laminated to the face of inner nonwoven material layer 56 facing away from outer meltblown fiber layer 55.

Users in the medical profession of medical garments and drapes have reported the tendency of medical instruments to slide when placed on such articles produced from conventional layered nonwoven materials where the outer layer is a spunbond layer. We have found that the material of this invention having an outer meltblown layer, while being resistant to abrasion, nevertheless has a higher static and dynamic coefficient of friction than spunbond. Indeed, tests conducted in accordance with the Standard Test Method for Static and Kinetic Coefficients of Friction of Plastic Film and Sheeting—ASTM Designation D-1894 show that the outer meltblown layer of the layered nonwoven material of this invention has a static coefficient of friction in the range of about 0.39 to 0.45 and a dynamic coefficient of friction in the range of about 0.29 to 0.33, compared to 0.29 to 0.31 and 0.20 to 0.21, respectively, for spunbond.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A diaper comprising:

a body side liner;

an outer cover comprising an outer meltblown fiber layer of a meltblown material having an average basis weight in a range of about 1 $g/m^2$ to about 7 $g/m^2$ disposed on an inner nonwoven material layer; and an absorbent material disposed between said body side liner and said outer cover.

2. A diaper in accordance with claim 1, wherein said basis weight of said meltblown fiber layer is in the range of about 3 $g/m^2$ to about 7 $g/m^2$.

3. A diaper in accordance with claim 1, wherein said basis weight of said meltblown fiber layer is about 5 $g/m^2$.

4. A diaper in accordance with claim 1, wherein the average basis weight of said outer cover is less than about 23 $g/m^2$.

5. A diaper in accordance with claim 1, wherein said inner nonwoven material layer is a spunbond.

6. A diaper in accordance with claim 5, wherein said spunbond has an average spunbond basis weight of about 17 $g/m^2$ and said average basis weight of said outer meltblown fiber layer is about 4 $g/m^2$.

7. A diaper in accordance with claim 1 further comprising a film layer disposed on an inner facing face of said nonwoven material layer.

8. A diaper in accordance with claim 7, wherein said film layer is a breathable film layer.

9. A diaper in accordance with claim 1, wherein said meltblown fiber layer is comprised of microfibers having a microfiber denier per filament of less than about 0.67.

10. A diaper in accordance with claim 9, wherein said microfiber denier per filament is less than about 0.06.

11. A diaper in accordance with claim 1, wherein said microfiber denier per filament is in a range of about 0.01 to about 0.67.

12. A diaper in accordance with claim 1, wherein said outer meltblown fiber layer has a uniformity such that no ½-inch diameter circle of said meltblown fiber layer has a basis weight of less than about 1 $g/m^2$ and greater than about 7 $g/m^2$.

13. A personal care article comprising:

a body side liner;

an outer cover comprising an outer meltblown fiber layer of a meltblown material having an average basis weight in a range of about 1 $g/m^2$ to about 7 $g/m^2$ disposed on an inner nonwoven material layer; and an absorbent material disposed between said body said liner and said outer cover.

14. A personal care article in accordance with claim 13, wherein said basis weight of said meltblown fiber layer is in the range of about 3 $g/m^2$ to about 7 $g/m^2$.

15. A personal care article in accordance with claim 13, wherein said basis weight of said meltblown fiber layer is about 5 $g/m^2$.

16. A personal care article in accordance with claim 13, wherein said inner nonwoven material layer is a spunbond.

17. A personal care article in accordance with claim 13, wherein said meltblown fiber layer is comprised of microfibers having a microfiber denier per filament of less than about 0.67.

18. A personal care article in accordance with claim 17, wherein said microfiber denier per filament is in a range of about 0.01 to about 0.67.

19. A personal care article in accordance with claim 13, wherein said personal care article is a training pants.

20. A personal care article in accordance with claim 13, wherein said personal care article is an adult incontinence garment.

* * * * *